(12) United States Patent
LeVert

(10) Patent No.: US 8,696,683 B2
(45) Date of Patent: Apr. 15, 2014

(54) APPARATUS FOR REMOVING AN OBJECT FROM A LUMEN

(76) Inventor: Francis Edward LeVert, Knoxville, TN (US)

( * ) Notice: Subject to any disclaimer, the term of this patent is extended or adjusted under 35 U.S.C. 154(b) by 81 days.

(21) Appl. No.: 12/586,534

(22) Filed: Sep. 24, 2009

(65) Prior Publication Data

US 2011/0071539 A1 Mar. 24, 2011

(51) Int. Cl.
*A61B 17/94* (2006.01)

(52) U.S. Cl.
USPC .......................................................... 606/113

(58) Field of Classification Search
USPC ......... 606/113, 114, 127, 128, 159, 151, 157, 606/158; 600/104–107, 121–125, 175; 24/545, 555, 564
See application file for complete search history.

(56) References Cited

U.S. PATENT DOCUMENTS

| | | | | |
|---|---|---|---|---|
| 3,946,877 | A * | 3/1976 | Galicia | 211/65 |
| 5,505,161 | A * | 4/1996 | Swendseid | 119/708 |
| 6,071,233 | A * | 6/2000 | Ishikawa et al. | 600/104 |
| 6,712,832 | B2 * | 3/2004 | Shah | 606/192 |
| 6,758,831 | B2 * | 7/2004 | Ryan | 604/103.03 |
| 2003/0195387 | A1 * | 10/2003 | Kortenbach et al. | 600/104 |
| 2005/0234297 | A1 * | 10/2005 | Devierre et al. | 600/153 |
| 2007/0232850 | A1 * | 10/2007 | Stokes et al. | 600/104 |
| 2008/0103357 | A1 * | 5/2008 | Zeiner et al. | 600/104 |
| 2008/0132758 | A1 * | 6/2008 | Stefanchik et al. | 600/104 |
| 2008/0277853 | A1 * | 11/2008 | Menn | 269/87 |

* cited by examiner

*Primary Examiner* — Ryan Severson
*Assistant Examiner* — Rachel S Papeika

(57) ABSTRACT

An extensible polyp retrieval apparatus designed to be slidably disposed along the outer surface of an endoscope that is fully or partially inserted in the lumen of a patient using a "connect and push" polyp retrieval apparatus to reach the distal end of the inserted endoscope. The polyp retrieval apparatus comprises: a flexible cylindrical polymeric tube capable of being deployed from a few centimeters in mounted length on an endoscope to over 210 centimeters in total length when partially deployed or fully extended, respectively; a multiplicity of clamping fasteners permanently mounted to the flexible cylindrical polymeric tube; a movable snare like device that is designed as an cooperating component of the polyp retrieval system to enable the grasping and storage of polyps therein so as to avoid the complete removal of the endoscope from the lumen as is normal to remove a large polyp after cauterization or after a piecemeal polypectomy. This is performed before continuing the inspection and removal process. The apparatus that is the subject of this invention will greatly improve this process and result in fewer chances for damage or injury to the patient along with the attendant cost benefits especially time saved in this medical procedure.

8 Claims, 4 Drawing Sheets

APPARATUS FOR REMOVING AN OBJECT FROM A LUMEN

TECHNICAL FIELD

The present invention relates to a post polypectomy polyp removal system. More particularly, the present invention relates to an apparatus for retrieving polyps that have been detached from the inner surface of a lumen via polypectomy maneuvers, without having to withdraw the endoscope after each polypectomy.

BACKGROUND DISCUSSION

If a polyp is found with any diagnostic modality, it must be removed and later tested in the pathology laboratory for signs of colorectal cancer. Polyps are routinely removed at the time of colonoscopy via suction aspiration via the suction channel of the scope. These are recovered in a polyp trap bottle. If unable to be aspirated, the large polyp is frequently suctioned to the end of the scope. The entire endoscope is withdrawn to remove the large polyp or it is recovered in a basket fed through the instrument channel. When a treatment tool such as a forcep or snare is inserted into a body channel through an instrument channel of an endoscope, the operator typically must perform the operation while holding the endoscope and treatment tool in their own hands while the treatment tool is being fed to the location in the lumen via the instrument channel. To avoid the intensive labor involved in the extraction and insertion of the treatment tool, Okada (U.S. Pat. No. 7,582,054, issued Sep. 1, 2009) teaches an extraction-insertion system which carries out feeding into or drawing out of a treatment tool through the instrument channel and a driving section that drives this insertion-retraction mechanism. The extraction-insertion system can greatly reduce the time required to insert and retract a snare device after the cauterization and removal of a polyp from the colon which can be as long as 2 meters but there is a need for a device that eliminates the need to retract the endoscope or the polypectomy tool before continuing the examination of the colon for additional polyps. At the discovery of multiple polyps in one site or after a piecemeal polypectomy, the scope must be removed and reinserted after each large polyp or piece is removed. It is an objective of this invention to provide an apparatus for removal of a multiplicity of polyps or pieces thereof without repeated endoscope insertion-retraction operations during the polyp or the piecemeal extraction removal process which is practiced at the present time. Further objectives will become apparent during the detailed discussion of the device of this invention.

DETAILED DESCRIPTION OF THE INVENTION

Figure 1:
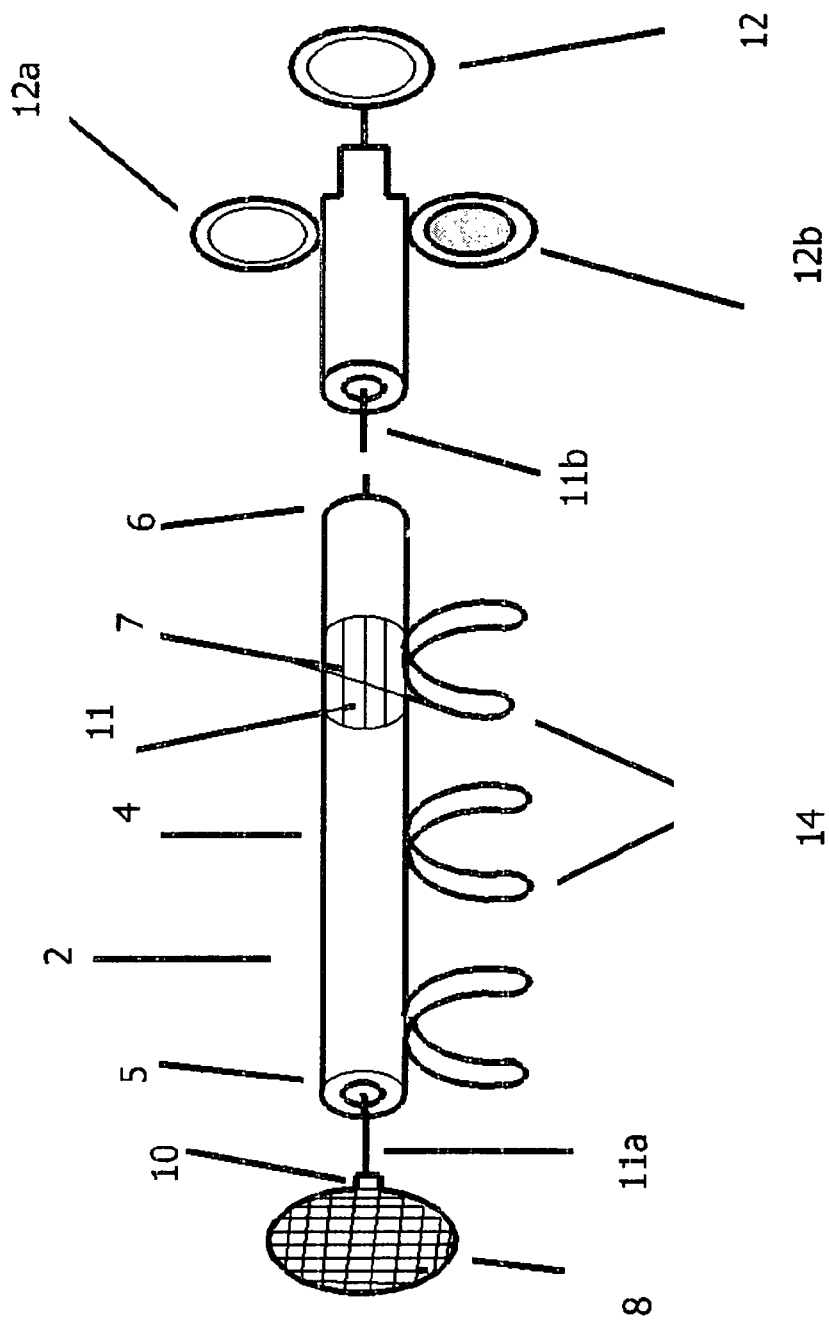
FIG. 1 is a side view of the polyp retrieval apparatus inch worm assembly of this invention with a polyp basket and associated wire, slide handle and finger grip inserted therein.

Referring now to the drawings and specific reference to FIG. 1, a medical device constructed in accordance with the teachings of this disclosure is generally referred by the numeral 2. FIG. 1 shows the first embodiment of an apparatus for collecting and removing polyps resulting from a polypectomy. The apparatus, hereafter referred to by the appellation "inch worm" and denoted by the numeral 2 in FIG. 1, comprises: Tubular member 4 with distal end 5 and proximal end 6 having a longitudinal channel 7 (this may be referred to as a "throughchannel" in this discussion) extending from the proximal end 6 through the distal end 5; A polyp removal instrument comprising a flexible polymeric polyp basket 8 connected to the terminal end 11a of traveling wire 11, via an inert material fastener 10, with the polyp basket 8 being held at an operational distance well beyond the distal end 5 of the tubular member 4; sliding/squeeze handle 12 in cooperation with finger grips 12a and 12b which are connected to the proximal end 11b of wire 11; and, a multiplicity of high strength polymeric clamping fasteners 14 permanently attached to tubular member 4 in a prescribed manner such that a plane containing the longitudinal central axis of the tubular member 4 divides the clamping fasteners into two equal halves, with the clamping fasteners being attached so as to allow slidable motion of the inch worm 2 along the circular longitudinal surface of the tubular 4. The high strength clamping fasteners 14 of the present invention were made of polyamide polymer material with an arc length of greater than 180 degrees such that the inch worm 2 can be easily attached and resist detachment from the exterior surface of a tubular host by an outwardly directed resultant normal force of less than 40 lbf. The design of the clamping fasteners is such that the friction between the inner surface of a lumen and the outer surface 24 and shape of the fasteners is minimal. The apparatus for removing polyps shown in FIG. 1 shows a polyp basket combined with a handle and connecting wire as the instrument employed with the tubular member, however, it could have been any instrument compatible with channel 7 and the process of polyp removal.

The sliding handle 12 is attached to the polyp basket 8, via the proximal end 11b of wire 11, and the distal end 11a of wire 11, respectively. The basket 8 may be used to collect several small polyps when the exact location of the collection site is not important or a large polyp that is removed by retracting only the inch worm 2 from the lumen thereby avoiding the retraction of the endoscope from the lumen. The sliding handle 12 with the cooperating finger grips 12a and 12b has a latching mechanism 19 (not shown in the figures} that allows the user to 'lock in" all severed polyps in basket 8 for removal from the lumen using inch worm 2.

Figure 2:
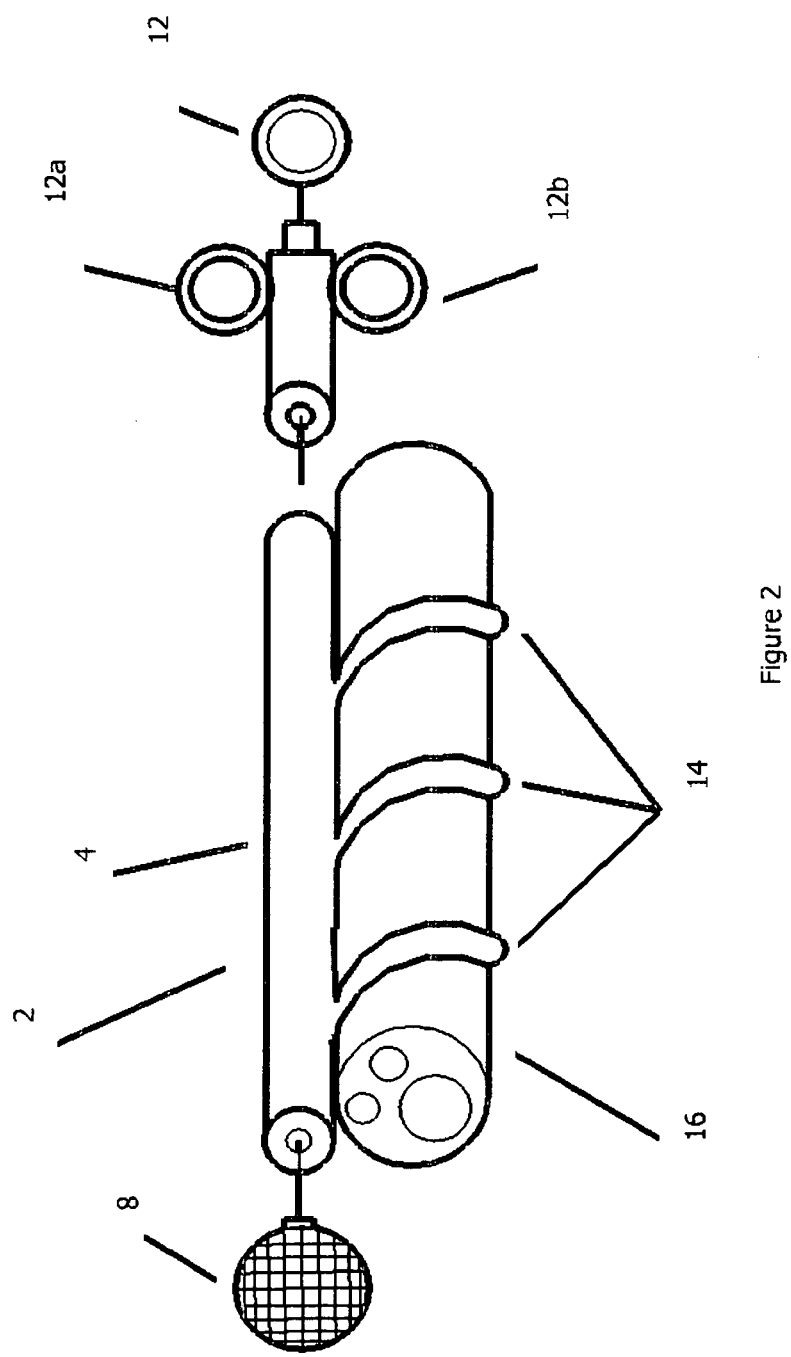
FIG. 2 shows a prospective view of the polyp retrieval apparatus as it would be deployed on an endoscope inserted in a lumen of a patient.

FIG. 2 shows a schematic drawing of the device of the first embodiment of the apparatus of this invention, inch worm 2, mounted on ordinary endoscope 16. The linear spacing of the clamping fasteners 14 and the flexibility of the tubular member 4 is such that the tubular member 4 and the fasteners 14 can remain in connected to the endoscope during its insertion through the bending, turning radiuses and kinking of the installed endoscope 16 which often occurs doing actual patient use. The endoscope has a lubricated latex coating which promotes the slidability of the clamping fasteners 14 of the attached inch worm 2. The polymer material used in the clamping fasteners was chosen from the class of high modulus and high strength linear polycondensates to enable the clamping fasteners to resist lost of encircling contact with the endoscope during insertion and removal of the inch worm 2. The inch worm 2 in FIG. 2 is shown as it would be installed manually on an endoscope that is inserted in a patient's lumen.

Additionally, the forward end of the inch worm 2 is designed such that it presents a non blunt edge to all of the body tissue it encounters while moving along the surface of the endoscope. Likewise, the clamping fasteners are designed to be free of blunt, sharp, or any protrusions that can cause trauma to tissue on the interior of the lumen. Tubular member 4 is made of a flexible non-toxic, and non hemolytic polymeric material such as TYGON (trademark). The terminal ends of clamping fasteners 14 are shown in FIG. 1 without the low friction polymeric tips 20 shown in FIG. 4. However the low friction polymeric tips 20 may be employed on all clamping fasteners used in both embodiments of this invention.

Figure 3:
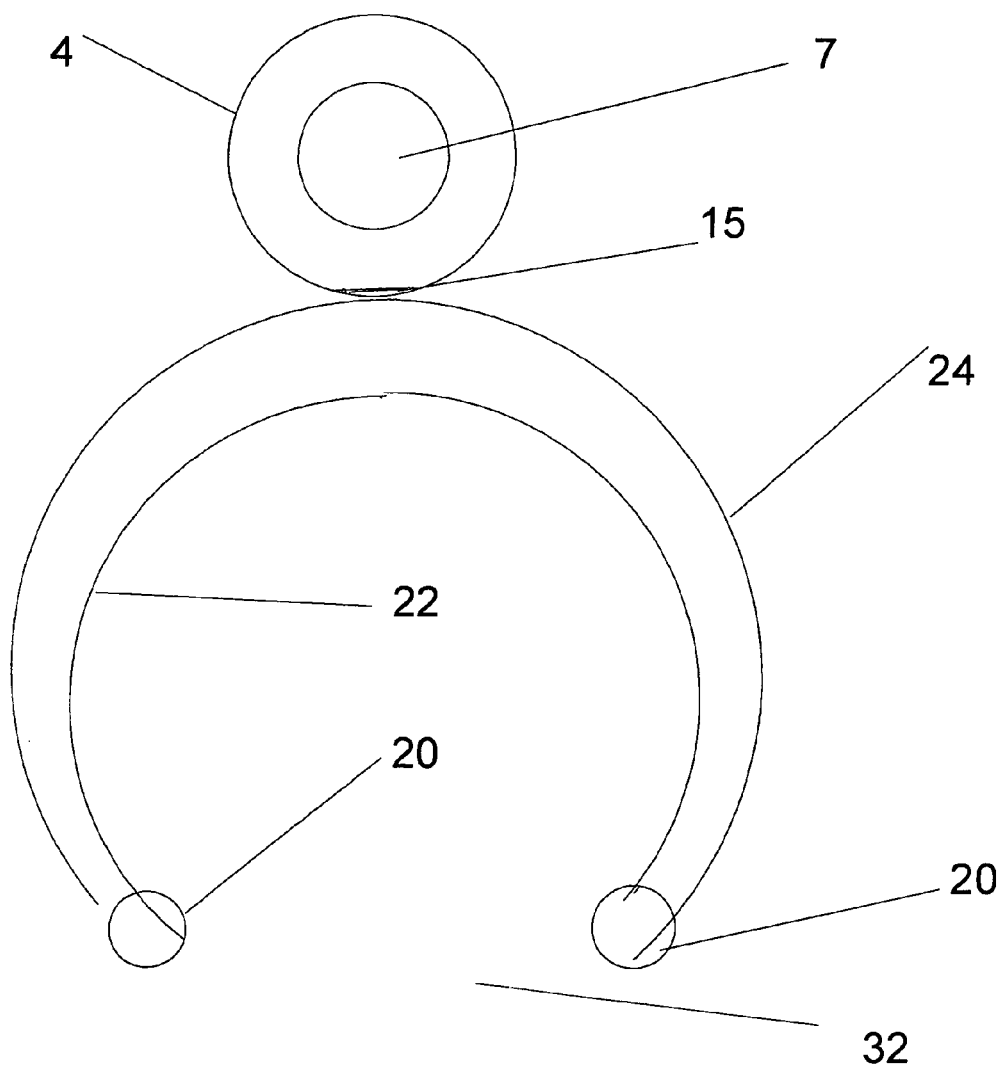
FIG. 3 shows a schematic representation of the clamping fastener designed to safely hold the polyp retrieval apparatus on the surface of the tubular member while enhancing and guiding its slidability along the surface of the endoscope.

FIG. 3 shows a schematic frontal representation of at least one of the multiplicity of clamping fasteners used to maintain essentially a constant distance between the center of the inch worm 2 and the outer surface of an endoscope. In FIG. 3, tubular member 4 is attached to the surface of clamping fastener, at its apex, by radio frequency (RF) welding of tubular member 4 to the apex of clamping fastener 14. Opening 32 of clamping fastener 14 is less than the diameter of endoscope 16. The opening 32 of clamping fastener 14 is designed to be less than 75 percent than the diameter of the endoscope such that is difficult to free a clamping fastener from the surface of the endoscope while inserting or removing the inch worm. The inch worm 2 is designed to be essentially free of high sliding friction between the inner surface 22 of the clamping fastener 14 and the lubricated surface of the endoscope. The terminal ends of the clamping fastener 14 are covered with low friction polymeric tips 20. The clamping fasteners 14 were attached to the tubular member 4 of this invention by RF welding. However, the selection of this method of adhering the clamping fasteners 14 to the Tubular member 4 does not mean that the components could not have been welded or attached by other methods or adhesive safe for use in the human body. Also, the two components could have been molded together as one integral unit as shown in FIG. 4.

Figure 4:
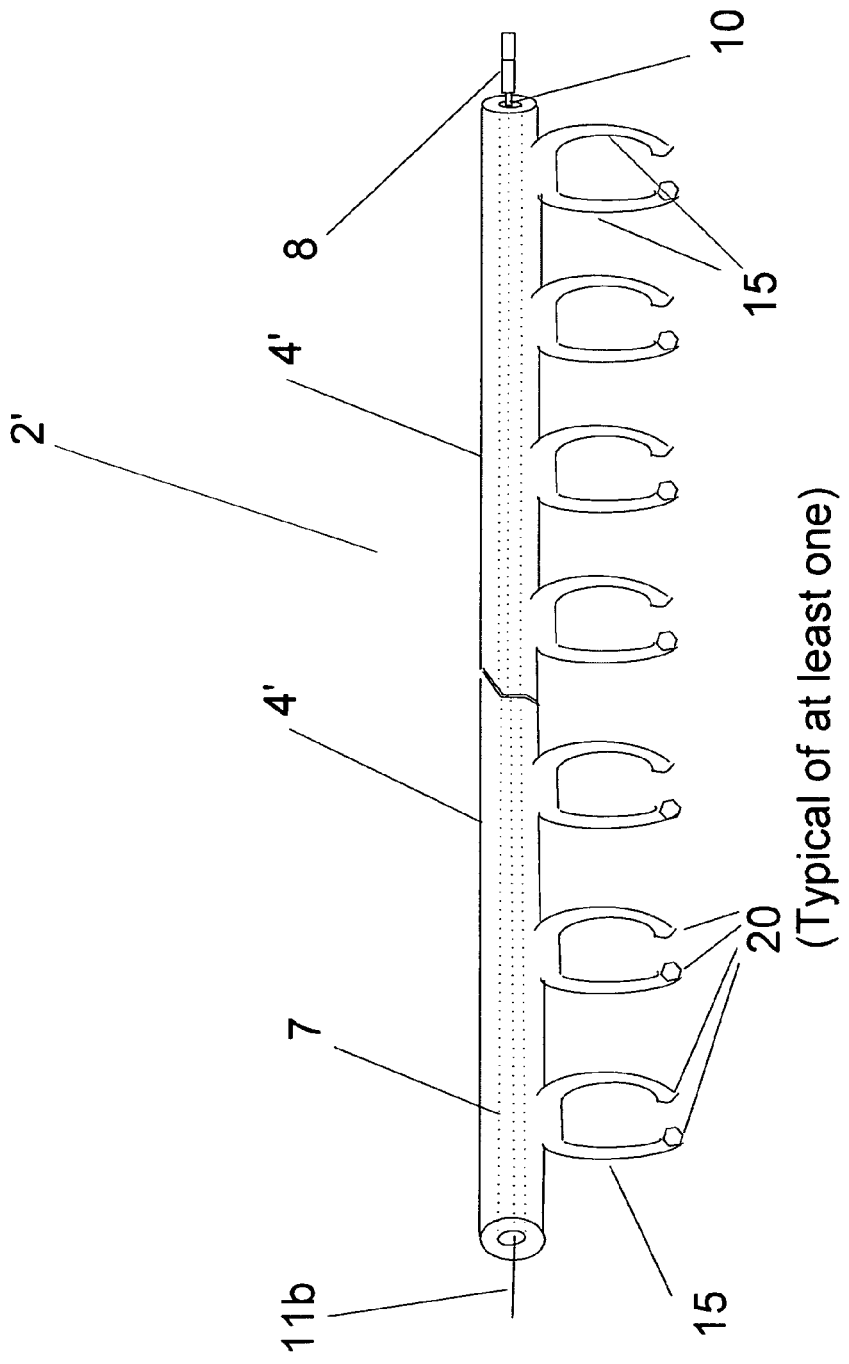
FIG. 4 is a schematic drawing of a section of a co-molded tubular member-clamping fastener system of the second embodiment of the device of this invention.

FIG. 4 shows a schematic representation of a section of the second embodiment of the inch worm 2' showing the tubular member 4' co-molded to at least one clamping fastener 15. The co-molded system provides a system with an almost fail safe junction between the fastener and the tubular member while at the same time maintaining the essential strength and modulus properties of each component.

The operation of the device of the subject invention will now be briefly explained. When a endoscope 16 is inserted in the lumen of a patient, the clamping fasteners 14 and the distal end of inch worm 2 are attached to the visible end of the endoscope by connecting a clamping fastener onto the endoscope and gently pushing the inch worm into the lumen. This action is repeated until the distal end of the inch worm extends beyond the distal and viewing end of the endoscope. At this point the operator can push the polyp basket out of the distal end of the tubular member and begin the collection and removal process.

What is claimed is:

1. An apparatus for use with an endoscope, said apparatus comprising:
   a tubular member of finite length having a channel that extends throughout said tubular member;
   a polyp basket, rigidly connected to a wire at the distal end of said tubular member that extends through said channel of the tubular member to slidably connect said polyp basket to sliding handle and griping means at the proximal end of the tubular member; and,
   a multiplicity of clamping fasteners, having arc lengths of greater than 180 degrees between their terminal ends, rigidly attached to the perimeter of the tubular member at prescribed intervals, said multiplicity of clamping fasteners having low friction rounded polymeric tips covering said terminal ends of the clamping fasteners to prevent trauma to tissue of a lumen during insertions and retractions and to promote sliding when attached to an endoscope.

2. The apparatus of claim 1 wherein said clamping fasteners consist of circular clamping fasteners with arc lengths of greater than a length defined by 180 degrees between the terminal ends, said arc length resulting in an opening there between of less than seventy five percent (i.e., 75%) of the diameter of an endoscope, said clamping fastener having low friction spherical polymeric tips covering the terminal ends of the clamping fasteners.

3. The apparatus of claim 1 wherein the terminal ends of the symmetrical projections of the clamping fasteners are structurally designed, based on their modulus properties, to resist attachment/detachment until a separation distance resulting from an applied resultant force, between their polymeric coverings is equal to or greater than the diameter of the endoscope.

4. The apparatus of claim 3 wherein said applied resultant force is greater than or equal to a the forty pound force needed to resist attachment and detachment of the clamping fasteners.

5. An apparatus for removing an object from a lumen while deployed on the surface of an endoscope, the apparatus comprising:
   a monolithic unit co-molded using composites of rigid and flexible polymeric materials to form said monolithic unit comprising a flexible tubular member, having a proximal end and a distal end, and at least one high strength polymeric clamping fastener, having high modulus properties said flexible tubular member of said monolithic unit, having a channel that extends the full length of the flexible tubular member; and,
   a polyp basket rigidly connected to a wire projecting into the distal end and through said channel in the tubular member to the proximal end of the channel in the flexible tubular member of the monolithic unit where it is connected to a controlling means for grasping objects with said polyp basket by controlling the movement thereof.

6. The apparatus of claim 5 wherein a multiplicity of high strength polymeric clamping fasteners with prescribed intervals there between are co-molded to the flexible tubular member to maintain sliding connectivity between the flexible tubular member and the endoscope during the movement of the apparatus on a deployed endoscope that has undergone the natural bending, turning radii and other departures from linearity during insertion.

7. A device comprising:
   a monolithic unit consisting of a flexible polymer tubular member with a through channel and clamping system having a multiplicity of high strength, high modulus fasteners co-molded to said flexible polymer tubular member with a high strength, high modulus properties polymer at fixed prescribed locations; and,
   a flexible polyp basket, a wire and a slidable squeeze handle, respectively, all mechanically, attached together to cooperatively remove detached polyps from a lumen via the through channel of said monolithic unit slidably mounted on a fully or partially inserted endoscope.

8. The apparatus of claim 7 wherein said clamping fasteners consist of circular clamping fasteners with arc lengths greater than a length defined by 180 degrees between the terminal ends of each clamping fastener, having rounded low friction polymeric coverings attached to the terminal ends of each clamping fastener.

* * * * *